US00PP33770P2

(12) United States Plant Patent
Kievit et al.

(10) Patent No.: US PP33,770 P2
(45) Date of Patent: Dec. 21, 2021

(54) ***PHLOX* PLANT NAMED 'BALKAPOSIN'**

(50) Latin Name: *Phlox paniculata*
Varietal Denomination: Balkaposin

(71) Applicant: Ball Horticultural Company, West Chicago, IL (US)

(72) Inventors: Christa Kievit, Hem (NL); Karl F. Batschke, Geneva, IL (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 17/460,270

(22) Filed: Aug. 29, 2021

(51) Int. Cl.
*A01H 5/02* (2018.01)
*A01H 6/70* (2018.01)

(52) U.S. Cl.
USPC ..... Plt./320

(58) Field of Classification Search
USPC ..... Plt./263.1, 320
See application file for complete search history.

*Primary Examiner* — Susan McCormick Ewoldt
*Assistant Examiner* — Karen M Redden
(74) *Attorney, Agent, or Firm* — Audrey Charles

(57) ABSTRACT

A new and distinct cultivar of *Phlox* plant named 'Balkaposin', characterized by its light pink-colored flowers with a red-purple center, medium green-colored foliage, and moderately vigorous, compact-upright growth habit, is disclosed.

1 Drawing Sheet

Latin name of genus and species of plant claimed: *Phlox paniculata.*

Variety denomination: 'Balkaposin'.

BACKGROUND OF THE INVENTION

The present invention relates to a new and distinct cultivar of *Phlox* plant botanically known as *Phlox paniculata* and hereinafter referred to by the cultivar name 'Balkaposin'.

The new cultivar originated in a controlled breeding program in Hem, the Netherlands during the summer of 2013. The objective of the breeding program was the development of *Phlox* cultivars with attractive flower coloration, increased powdery mildew resistance and a compact-upright growth habit.

The new *Phlox* cultivar is the result of open-pollination. The female (seed) parent of the new cultivar is the proprietary *Phlox paniculata* breeding selection coded E04-14, not patented, characterized by its light rose-colored flowers, medium green-colored foliage, and moderately vigorous, upright growth habit. The male (pollen) parent of the new cultivar is unknown. The new cultivar was selected as a single flowering plant within the progeny of the above stated open-pollination during July 2014 in a controlled environment in Hem, the Netherlands.

Asexual reproduction of the new cultivar by terminal stem cuttings since July 2014 in Hem, the Netherlands and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balkaposin' as a new and distinct cultivar of *Phlox* plant:

1. Light pink-colored flowers with a red-purple center;

2. Medium green-colored foliage; and
3. Moderately vigorous, compact-upright growth habit.

Plants of the new cultivar differ from plants of the female parent primarily in having lighter, pink-colored flowers.

Of the many commercially available *Phlox* cultivars, the most similar in comparison to the new cultivar is KA-POW White Bicolor 'Balkapowibi', U.S Plant Pat. No. 30,782. However, in side-by-side comparisons, plants of the new cultivar differ from plants of 'Balkapowibi' in at least the following characteristics:

1. Plants of the new cultivar have larger primary inflorescences than plants of 'Balkapowibi';
2. Plants of the new cultivar have more flowers per primary inflorescence than plants of 'Balkapowibi'; and
3. Plants of the new cultivar have pink-colored flowers unlike plants of 'Balkapowibi'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balkaposin'. The plants were approximately seven months old. The plants were grown for approximately 13 weeks in an outdoor garden-type bed in West Chicago, Ill.

DETAILED BOTANICAL DESCRIPTION

Figure 1:
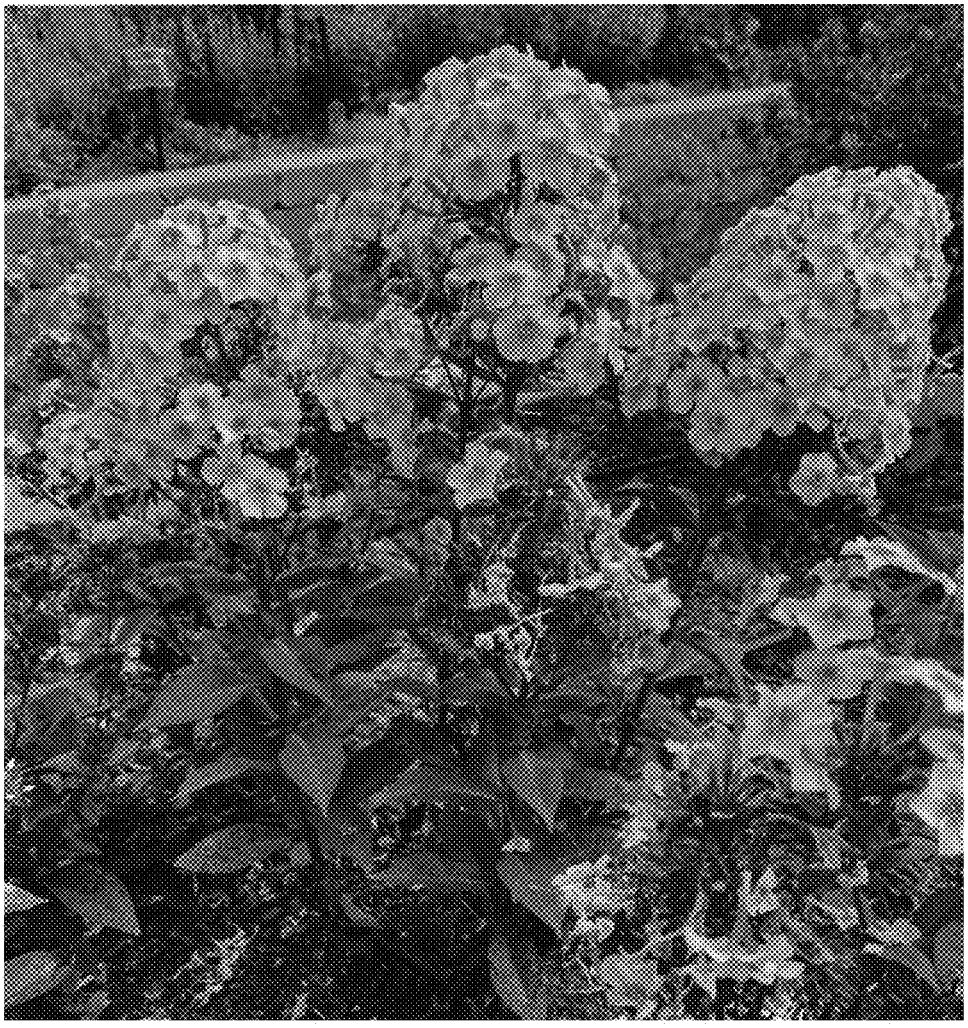
FIG. 1 illustrates a side view of the overall growth and flowering habit of 'Balkaposin'.
Figure 2:
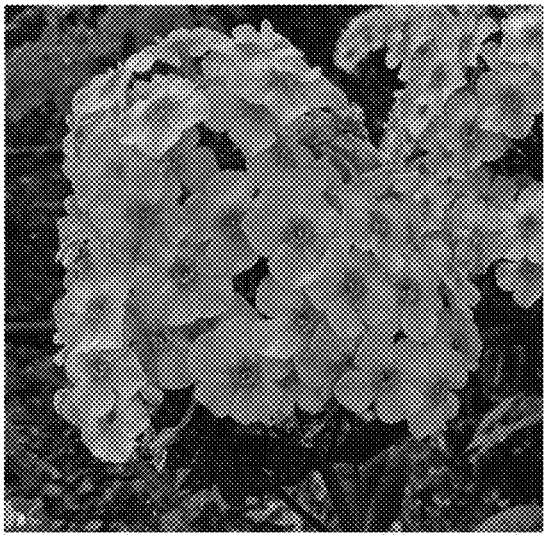
FIG. 2 illustrates a close-up view of an individual inflorescence of 'Balkaposin'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The RHS Colour Chart of The Royal Horticultural Society, London, England, 2015 edition, except where general color terms of ordinary significance are used. The color values were determined in August 2021 under natural light conditions in Naperville, Ill.

The following descriptions and measurements describe approximately seven-month-old plants produced from cuttings from stock plants and grown under conditions comparable to those used in commercial practice. Rooted cuttings were transplanted in one-gallon containers and grown in a poly-covered greenhouse in West Chicago, Ill. Plants were given one pinch four weeks after transplant. After approximately 11 weeks, plants were then transplanted in an outdoor garden-type bed in West Chicago, Ill. and grown for approximately 13 weeks. Greenhouse temperatures ranged from an average high of an average high of 60.0° F. (15.6° C.) to an average low of 51.5° F. (10.3° C.). No supplemental lighting was provided. Measurements and numerical values represent averages of typical plants.

Botanical classification: *Phlox paniculata* 'Balkaposin'.

Parentage:

*Female parent.*—Proprietary *Phlox paniculata* breeding selection coded E04-14, not patented.

*Male parent.*—Unknown.

Propagation:

*Type cutting.*—Terminal stem.

*Time to initiate roots.*—Approximately 10 to 12 days.

*Time to produce a rooted cutting.*—Approximately 42 to 49 days.

*Root description.*—Fine to medium thickness.

*Rooting habit.*—Freely branching, medium density.

Plant description:

*Commercial crop time.*—Approximately 10 to 12 weeks from a rooted cutting to finish in a 15 cm pot.

*Growth habit and general appearance.*—Herbaceous perennial, moderately vigorous, compact-upright growth habit.

*Hardiness.*—USDA Zone 4b (−25° F. to −20° F./−31.7° C. to −28.9° C.).

*Size.*—Height: Approximately 39.0 cm. Width: Approximately 31.0 cm.

*Branching habit.*—Freely branching, pinching will improve branching.

*Branch.*—Quantity: Approximately 6 basal branches. Shape: Round. Strength: Strong. Length to base of inflorescence: Approximately 28.0 cm. Diameter: Approximately 3.0 mm to 4.0 mm. Length of central internode: Approximately 2.2 cm. Texture: Glabrous. Color of young stems: 146C. Color of mature stems: 146B, becoming woody 199B with age.

Foliage description:

*General description.*—Quantity of leaves per main branch: Approximately 14. Fragrance: None detected. Form: Simple. Arrangement: Opposite, decussate.

*Leaves.*—Shape: Elliptic, slightly carinate. Margin: Entire, minutely ciliate. Apex: Acute. Base: Attenuate. Venation pattern: Pinnate. Length: Approximately 6.7 cm. Width: Approximately 3.0 cm. Texture of upper surface: Sparsely pubescent. Texture of lower surface: Glabrous. Color of upper surface of young and mature foliage: Closest to 137A with venation of 146D. Color of lower surface of young and mature foliage: Closest to 147B with venation of 146D.

*Petioles.*—Length: Approximately 2.0 mm. Width: Approximately 2.0 mm to 3.0 mm. Texture: Glabrous. Color: 146D.

Flowering description:

*Flowering habit.*—'Balkaposin' is a long day obligate and is freely flowering under outdoor growing conditions with substantially continuous blooming from late spring throughout summer.

*Lastingness of individual flower on the plant.*—Approximately 10 days.

Inflorescence description:

*General description.*—Type: Compound terminal panicle, flowers face upright and outwardly, self-cleaning. Quantity per plant: Approximately 5. Fragrance: Moderately sweet and pleasant. Height of primary: Approximately 10.0 cm. Width of primary: Approximately 11.0 cm. Quantity of fully open flowers per primary inflorescence: Approximately 45. Height of secondary: Approximately 5.0 cm. Width of secondary: 7.0 cm. Quantity of fully open flowers per secondary inflorescence: Approximately 10.

*Peduncle.*—Strength: Strong. Aspect: Primary erect, axillary acute angle to stem. Length of primary: Approximately 2.0 cm. Diameter of primary: Approximately 2.0 mm to 3.0 mm. Length of axillary: Approximately 3.5 cm to 5.5 cm. Diameter of axillary: Approximately 1.5 mm. Texture: Densely pubescent. Color: 146C occasionally tinted with N186A.

Flower description:

*Type.*—Single.

*Bud.*—Rate of opening: Generally takes 3 to 4 days for bud to progress from first color to fully open flower.

*Bud just before opening.*—Shape: Oblanceolate. Length: Approximately 1.4 cm. Diameter: Approximately 4.0 mm. Color: Calyx of 145B with a central streak of N186A and petal portion of NN155A with an overlay of 75B.

*Corolla.*—Shape: Salverform. Diameter: Approximately 2.3 cm. Depth: Approximately 2.4 cm.

*Petals.*—Quantity: 5 in a single whorl, base fused into a narrow tube. Lobe shape: Obovate. Margin: Entire. Apex: Broadly acute to obtuse. Lobe length: Approximately 1.0 cm. Lobe width: Approximately 1.2 cm. Texture of upper and lower surfaces: Smooth, glabrous. Color of upper surface when first open: NN155D with an overlay of N74D, orifice of N74A. Color of lower surface when first open: NN155D with an underlay of N74D. Color of upper surface when fully open: NN155D with an overlay of N74D, orifice of N74B. Color of lower surface when fully open: NN155D with a faint underlay of N74D.

*Corolla tube.*—Length: Approximately 2.1 cm. Diameter at distal end: Approximately 2.0 mm. Diameter at proximal end: Approximately 2.0 mm. Texture of outer surface: Sparsely pubescent. Texture of inner surface: Smooth, glabrous with 3.0 mm densely pubescent patch near base. Color of inner surface: 155D with 77A at throat opening. Color of outer surface: 77B with 155D at base.

*Calyx.*—Shape: Cupped. Length: Approximately 6.0 mm. Diameter: Approximately 2.0 mm.

*Sepals.*—Quantity per flower: 5, lower half fused. Shape: Lanceolate. Apex: Narrowly apiculate. Length: Approximately 9.0 mm. Width: Approximately 2.0 mm. Texture of outer surface: Sparsely pubescent. Texture of inner surface: Smooth, glabrous. Color of inner surface: 145B with tip and thin central streak on upper half of N186A. Color of outer surface: 145B with tip of and central streak of N186A.

*Pedicel.*—Strength: Strong, flexible. Aspect: Primary erect, axillary acute angle to peduncle. Length: Approximately 5.0 mm. Diameter: Approximately 1.0 mm. Texture: Densely pubescent. Color: 146C occasionally tinted with N186A.

*Reproductive organs.*—Androecium: Stamen quantity: 5 per flower, adnate to corolla tube. Stamen length: Approximately 2.0 cm. Filament length of free portion: Approximately 1.0 mm. Anther shape: Sagittate. Anther length: Approximately 2.0 mm. Anther color: 155A. Pollen amount: Abundant. Pollen color: 155D. Gynoecium: Pistil quantity: 1 per flower. Pistil length: Approximately 1.8 cm. Stigma shape: Cleft, three-parted. Stigma color: 145C. Style length: Approximately 1.6 cm. Style color: 145D with an overlay of 77A. Ovary length: Approximately 2.0 mm. Ovary color: 144A.

Seed and fruit production: Neither seed nor fruit production has been observed.

Disease and pest resistance: Increased resistance to powdery mildew has been observed.

What is claimed is:

1. A new and distinct cultivar of *Phlox* plant named 'Balkaposin', substantially as herein illustrated and described.

* * * * *